(12) United States Patent
Aouad et al.

(10) Patent No.: US 10,538,631 B2
(45) Date of Patent: *Jan. 21, 2020

(54) BENEFIT AGENT CONTAINING DELIVERY PARTICLE

(71) Applicant: The Procter & Gamble Company, Cincinnati, OH (US)

(72) Inventors: Yousef Georges Aouad, Cincinnati, OH (US); Johan Smets, Lubbeek (BE); Luke Andrew Zannoni, West Chester, OH (US); Piero Baglioni, Fiesole (IT); Paolo Tempesti, Prato (IT); Arianna Bartolini, Florence (IT)

(73) Assignee: The Procter & Gamble Company, Cincinnati, OH (US)

(*) Notice: Subject to any disclaimer, the term of this patent is extended or adjusted under 35 U.S.C. 154(b) by 17 days.

This patent is subject to a terminal disclaimer.

(21) Appl. No.: 15/702,801

(22) Filed: Sep. 13, 2017

(65) Prior Publication Data

US 2018/0071201 A1    Mar. 15, 2018

Related U.S. Application Data

(60) Provisional application No. 62/393,821, filed on Sep. 13, 2016.

(51) Int. Cl.
| | |
|---|---|
| *C08G 81/02* | (2006.01) |
| *A61K 8/02* | (2006.01) |
| *A61K 8/91* | (2006.01) |
| *A61Q 5/12* | (2006.01) |
| *A61Q 19/00* | (2006.01) |
| *C11D 3/37* | (2006.01) |
| *C11D 3/50* | (2006.01) |
| *A61Q 5/02* | (2006.01) |
| *C11D 3/42* | (2006.01) |
| *C11D 17/00* | (2006.01) |

(52) U.S. Cl.
CPC .......... *C08G 81/025* (2013.01); *A61K 8/0241* (2013.01); *A61K 8/0291* (2013.01); *A61K 8/91* (2013.01); *A61Q 5/02* (2013.01); *A61Q 5/12* (2013.01); *A61Q 19/00* (2013.01); *C11D 3/373* (2013.01); *C11D 3/3788* (2013.01); *C11D 3/42* (2013.01); *C11D 3/505* (2013.01); *C11D 17/0039* (2013.01); *A61K 2800/56* (2013.01)

(58) Field of Classification Search
CPC .... A61K 8/91; A61K 8/0291; A61K 2800/56; A61K 8/0241; C08G 81/025; C11D 3/3788; C11D 17/0039; C11D 3/505
See application file for complete search history.

(56) References Cited

U.S. PATENT DOCUMENTS

| | | | |
|---|---|---|---|
| 6,328,988 B1 * | 12/2001 | Uhrich | A61K 9/0014 424/422 |
| 7,851,543 B2 | 12/2010 | Emrick et al. | |
| 2004/0266655 A1 | 12/2004 | Baum | |
| 2008/0255326 A1 | 10/2008 | Widmaier | |
| 2009/0176935 A1 | 7/2009 | Boeckh et al. | |
| 2010/0204425 A1 | 8/2010 | Mertoglu | |
| 2012/0141796 A1 | 6/2012 | Adamson et al. | |
| 2013/0150277 A1 | 6/2013 | Fischer | |
| 2014/0065234 A1 | 3/2014 | Shum et al. | |
| 2015/0038394 A1 | 2/2015 | Tantawy | |
| 2016/0362644 A1 | 12/2016 | Meine | |
| 2018/0305636 A1 | 10/2018 | Kolter | |

FOREIGN PATENT DOCUMENTS

| | | |
|---|---|---|
| EP | 2334776 B1 | 8/2010 |
| EP | 3126478 B1 | 9/2018 |
| WO | WO2007/051743 A2 | 5/2007 |
| WO | WO2009013202 A1 | 1/2009 |

OTHER PUBLICATIONS

Bartolini, "Encapsulation of small molecules by poly(ethylene glycol)-graft-poly(vinyl acetate) unimer micelles", Jun. 1, 2016, https://ecis2016.org/sites/default/files/abstracts/Bartolini.pdf.
Bin Li et al., "A novel amphiphilic copolymer poly(ethylene oxide-co-ally1glucide1ether)-graft-poly([epsilon]-caprolactone): synthesis, self-assembly, and protein encapsulation behavior", Polymer Chemistry, vol. 3, No. 9, Jan. 1, 2012, pp. 2421-2429.
Bradley, "Chemistry at the polymer-particle interface for the design of innovative materials", Soft Matter, 2012, 8, pp. 1268-1274.
International Search Report and Written Opinion dated Nov. 23, 2017, U.S. Appl. No. 15/702,794, 10 pgs.
International Search Report and Written Opinion dated Nov. 23, 2017, U.S. Appl. No. 15/702,801, 12 pgs.
VanHecke, "Jamming of Soft Particles: Geometry, Mechanics, Scaling and isostaticity", arXiv:0911.1384v1 Nov. 7, 2009, 25 pgs.
Yow et al., "Formation of liquid core—polymer shell microcapsules", Soft Matter, 2006, 2, pp. 940-949.
Bartolini, Arianna et al.; Poly(ethylene glycol)-graft-poly(vinyl acetate) single-chain nanoparticles for the encapsulation of small molecules; Phys. Chem. Chem. Phys.; Jan. 17, 2017; vol. 19; pp. 4553-4559.
U.S. Appl. No. 15/702,794, filed Sep. 13, 2017, Yousef Georges Aouad et al.

(Continued)

*Primary Examiner* — Kortney L. Klinkel
(74) *Attorney, Agent, or Firm* — Gregory S. Darley-Emerson

(57) ABSTRACT

The present invention relates to benefit agent containing delivery particles, compositions comprising said particles, and processes for making and using the aforementioned particles and compositions. When employed in compositions, for example, cleaning or fabric care compositions, such particles increase the efficiency of benefit agent delivery, thereby allowing reduced amounts of benefit agents to be employed. In addition to allowing the amount of benefit agent to be reduced, such particles allow a broad range of benefit agents to be employed.

39 Claims, No Drawings

(56) References Cited

OTHER PUBLICATIONS

Polymersomes by Microfluidics; Douglas Adamson—Princeton University; adamson@princeton.edu; https://engineering.princeton.edu/news/2007/03/02/innovation-forum-highlights-rich-range-research; posted Mar. 2, 2007; downloaded Oct. 4, 2019.

\* cited by examiner

BENEFIT AGENT CONTAINING DELIVERY PARTICLE

FIELD OF INVENTION

The present application relates to benefit agent containing delivery particles, compositions comprising such particles, and processes for making and using such particles and compositions.

BACKGROUND OF THE INVENTION

Benefit agents, such as perfumes, silicones, waxes, flavors, vitamins and fabric softening agents, are expensive and/or can react with other active ingredients in the composition, for example, personal care compositions, cleaning compositions, and fabric care compositions. As a result, there is a desire to maximize the stability in the final composition of such benefit agents. One method of achieving such objective is to improve the delivery efficiencies of such benefit agents by encapsulating such benefit agents. Unfortunately, encapsulation processes are time consuming and expensive as they typically require chemical reactions such as extensive crosslinking and/or result in capsules that over protect the benefit agent as such capsules typically require a high energy input to release their active—for example pressure, temperature and/or electromagnetic radiation. Furthermore, such encapsulates' shell typically only protects the benefit agent and, on its own, provides no active value and can even be a negative as such encapsulate's cross-linked shell may leave a residue when a product containing the encapsulate is used.

Thus, what is needed is benefit agent containing delivery particles that can be formed without a crosslinking reaction, that release their benefit agent via the simple dilution of the product matrix in which the particles are contained and preferably comprise at least one self-assembling graft co-polymer that can provide a treatment benefit in addition and/or supplementary to the benefit provided by the benefit agent containing delivery particles' benefit agent. What is furthermore desired is using the same polymeric materials to deliver a wide variety of actives with different chemical and physical properties. Furthermore, a tunable delivery particle depending on the delivery needs, whereby specific polymeric delivery materials can be tuned into different delivery systems by the dictation of the specific environmental factors like water content, adjuncts types and levels, and the use of hydrophilic materials. What is furthermore desired is a particle which forms spontaneously when little energy is provided to the system, as for low shear mixing needed to ensure homogeneous distribution of the benefit agent particle within the composition.

Such benefit agent containing delivery particles and methods of making and using same are provided herein.

SUMMARY OF THE INVENTION

The present invention relates to benefit agent containing delivery particles comprising a benefit agent and at least one graft co-polymer carrier material, said benefit agent particles comprising at least one region comprising benefit agent, said at least one region comprising benefit agent being encompassed within said at least one graft co-polymer carrier material and/or being partially embedded within said at least one graft co-polymer carrier material, said benefit agent delivery particles The present invention also relates to compositions comprising said particles, and processes for making and using such particles and compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrance (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various pouches, tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof. The form of such compositions includes liquids, gels, beads, powders, flakes, and granules.

As used herein the term "unit dose article" means powder or solid detergent in a water soluble film.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A. A composition comprising:
a) a benefit agent delivery particles, said benefit agent delivery particles comprising at least one self-assembling graft co-polymer and a benefit agent, said benefit agent being encapsulated in said at least one self-assembling graft co-polymer, and/or being partially embedded in said at least one self-assembling graft co-polymer, preferably said at least one self-assembling graft co-polymer having hydrodynamic diameter of from about 10 nanometers to about 100 nanometers, more preferably from about 15 nanometers to about 80 nanometers, most preferably from about 20 nanometers to about 60 nanometers
b) an adjunct material
c) a free water level of 96% or less, preferably 90% or less, more preferably form about 5% to 90%, preferably when said composition is:
  (i) a unit dose composition, said free water is from about 5% to about 10%;
  (ii) a liquid detergent, said free water is from about 10% to about 70%;
  (iii) a liquid fabric enhancer, said free water is from about 80% to about 95%;
  (iv) a surface care cleaning composition, said free water is from about 85% to about 96%;
  (v) a skin care composition, said free water is from about 20% to about 96%;
  (vi) a hair cleaning and/or conditioning composition, said free water is from about 20% to about 96%
is disclosed.

B. A composition according to Paragraph A, wherein said benefit agent delivery particles have a self-assembly index of 1 to about 100 and/or a SAXS index of 1 to about 100 is disclosed.

C. Benefit agent delivery particles comprising a benefit agent and at least one self-assembling graft co-polymer, said benefit agent delivery particles having a Dissolution Index of 1, preferably said benefit agent particles comprising at least one region comprising benefit agent, said at least one region comprising benefit agent being encompassed within said at least one self-assembling graft co-polymer and/or being partially embedded within said at least one self-assembling graft co-polymer are disclosed.

D. Benefit agent delivery particles comprising a benefit agent and at least one self-assembling graft co-polymer, said benefit agent delivery particles having a self-assembly index of 1 to about 100 and/or a SAXS index of 1 to about 100 preferably said benefit agent particles comprising at least one region comprising benefit agent, said at least one region comprising benefit agent being encompassed within said at least one self-assembling graft co-polymer and/or being partially embedded within said at least one self-assembling graft co-polymer are disclosed.

E. Benefit agent delivery particles according to any of Paragraphs C through D, said benefit agent particles having a structure selected from the group consisting of:
a) a benefit agent particle comprising a single region of benefit agent that is embedded in said at least one self-assembling graft co-polymer;
b) a benefit agent particle comprising at least two regions of benefit agent that are embedded in said at least one self-assembling graft co-polymer;
c) a benefit agent particle comprising at least one region of benefit agent that are at least partially embedded on the surface said at least one self-assembling graft co-polymer;
d) a benefit agent particle comprising a single region of benefit agent that is embedded in said at least one self-assembling graft co-polymer and at least one region of benefit agent that is at least partially embedded on the surface said at least one self-assembling graft co-polymer; and
e) a benefit agent particle comprising at least two regions of benefit agent that are embedded in said at least one self-assembling graft co-polymer and at least one region of benefit agent that is at least partially embedded on the surface said at least one self-assembling graft co-polymer
are disclosed.

F. Benefit agent delivery particles according to any of Paragraphs C through E, said benefit agent particles having at least one particle having:
a) a diameter of from about 0.5 microns to about 5000 microns, preferably from about 0.5 microns to about 1000 microns, more preferably from about 0.5 microns to about 250 microns, most preferably from about 1 microns to about 60 microns;
b) a diameter of from about 0.01 microns to about 0.5 microns, preferably from about 0.02 microns to about 0.5 microns, more preferably from about 0.04 microns to about 0.5 microns; or
c) a diameter of from about 250 microns to about 10,000 microns, preferably from about 250 microns to about 7500 microns, more preferably from about 500 microns to about 5000 microns, most preferably from about 750 microns to about 2500 microns
are disclosed.

G. Benefit agent delivery particles according to any of Paragraphs C through F wherein the weight ratio of benefit agent to said at least one self-assembling graft co-polymer is from 1:20 to 20:1, preferably the ratio of benefit agent to said at least one self-assembling graft co-polymer is from 4:1 to 20:1 are disclosed. The weight ratio is the ratio between the total weight of the benefit agents and the total weight of the co-polymers.

H. Benefit agent delivery particles according to any of Paragraphs C through G wherein said benefit agent selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti skin aging agents, facial contrast agents, anti dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents and mixtures thereof, are disclosed.

I. Benefit agent delivery particles according to any of Paragraphs C through H wherein said at least one self-assembling graft co-polymer has a surface energy of from about 20 to about 90, preferably from about 20 to about 75, more preferably from about 20 to about 50 are disclosed.

J. The benefit agent particles according to any of Claims C through I wherein said at least one self-assembling graft co-polymer comprises a co-polymer of polyalkylene glycol and vinyl acetate having:
  a) a weight-average molecular weight of from about 2000 Daltons to about 250,000 Daltons, preferably from about 3000 Daltons to about 100,000 Daltons, more preferably 4,000 Daltons to about 50,000 Daltons, most preferably from about 5,000 to about 20,000 Daltons, and
  b) a ratio of polyalkylene glycol to vinyl acetate moieties of about 5:1 to about 1:10 preferably from about 3:1 to about 1:8, more preferably from about 2:1 to about 1:6 preferably said polyalkylene glycol comprises a material selected from the group consisting of polyethylene glycol, polypropylene glycol, polybutylene glycol and mixtures thereof, more preferably said polyalkylene glycol comprises polyethylene glycol, are disclosed.

K. The benefit agent particles according to any of Paragraphs C through J wherein said at least one self-assembling graft co-polymer comprises a co-polymer of polyalkylene glycol and vinyl acetate that comprises a polyalkylene glycol backbone comprising vinyl acetate moieties that are covalently attached to said polyalkylene glycol backbone, preferably said co-polymer of polyalkylene glycol comprises polyethylene glycol.

L. The benefit agent particles according to any of Paragraphs C through K wherein said at least one self-assembling graft co-polymer comprises a co-polymer of polyalkylene glycol and vinyl acetate has from 1 to about 10 vinyl acetate grafts per polyalkylene glycol backbone, preferably said co-polymer of polyalkylene glycol and vinyl acetate has from 1 to about 5 vinyl acetate moieties per polyalkylene glycol backbone, more preferably said co-polymer of polyalkylene glycol and vinyl acetate has from about 1 to about 3 vinyl acetate grafts per polyalkylene glycol backbone, most preferably said co-polymer of polyalkylene glycol and vinyl acetate has 1 vinyl acetate graft per polyalkylene glycol backbone, preferably said co-polymer of polyalkylene glycol comprises polyethylene glycol are disclosed.

M. The benefit agent particles according to any of Paragraphs C through L wherein said at least one self-assembling graft co-polymer comprises polyalkylene glycol and at least one monomer selected from the group consisting of vinyl esters, alkyl acrylates, alkyl methacrylates, alkyl acrylamides, alkyl methacrylamides, styrenes, halogenated olefins, and mixtures thereof, preferably said co-polymer of polyalkylene glycol comprises polyethylene glycol.

N. A composition comprising the benefit agent particles of any Paragraphs C through M said composition having a free water level of 96% or less, preferably 90% or less, more preferably form about 5% to 90%, preferably when said composition is:
  a) a unit dose composition, said free water is from about 5% to about 10%;
  b) a liquid detergent, said free water is from about 10% to about 70%;
  c) a liquid fabric enhancer, said free water is from about 80% to about 95%;
  d) a surface care cleaning composition, said free water is from about 85% to about 96%;
  e) a skin care composition, said free water is from about 20% to about 96%;
  f) a hair cleaning and/or conditioning composition, said free water is from about 20% to about 96%;
preferably said at least one self-assembling graft co-polymer has a hydrodynamic diameter of from about 10 nanometers to about 100 nanometers, more preferably from about 15 nanometers to about 80 nanometers, most preferably from about 20 nanometers to about 60 nanometers, is disclosed.

O. A composition according Paragraph N, said composition comprising, based on total composition weight from about 0.1% to about 25%, preferably from about 0.5% to about 20% of a surfactant selected from the group consisting of a cationic surfactant, an anionic surfactant, a nonionic surfactant and mixtures thereof, preferably said surfactant comprises a nonionic surfactant, more preferably said surfactant comprises 5% to about 25% of said nonionic surfactant, is disclosed.

P. A composition according to any of Paragraphs N through 0, comprising a water binding agent, preferably said compositions comprises based on total composition weight, from about 0.1% to about 50%, preferably from about 1% to about 15%, more preferably from about 2% to about 5%, preferably said water binding agent is selected from the group consisting of organic acids, salts of organic acids, humectants, desiccants, natural sugar substitutes, artificial sugar substitutes, hydrogels and mixtures thereof, is disclosed.

Q. A composition according to any of Paragraphs Claim N through P wherein said composition comprises, based on total composition weight, from about 5% to about 20%, from about 8% to about 15%, from about 9% to about 13% free water said composition being encased in a film, preferably said film comprises polyvinylalcohol, is disclosed.

R. A composition according to any of Paragraphs N through Q, said composition comprising a liquid and/or gel and a film, said film encasing said liquid and/or gel, optionally said liquid or gel comprises a suspended solid, is disclosed.

S. A composition according to any of Claims N through Q, said composition comprising based on total composition weight, from about 5% to about 95% free water and from about 0.5% to about 25% of a builder, is disclosed.

T. A composition according to any of Claims N through S, comprising, based on total composition weight, a material selected from the group consisting of a hueing dye, a structurant, an additional perfume delivery system and mixtures thereof; preferably.
  a) said structurant comprises a material selected from the group consisting of polysaccharides, preferably said polysaccharides are selected from the group consisting of modified celluloses, chitosan, plant cellulose, bacterial cellulose, coated bacterial cellulose, preferably said bacterial cellulose comprises xathan gum; castor oil, hydrogenated castor oil, modified proteins, inorganic salts, quaternized polymeric materials, imidazoles; nonionic polymers having a pKa less than 6.0, polyurethanes, non-polymeric crystalline hydroxyl-functional materials, polymeric structuring agents, di-amido gellants, a homopolymer of Formula (Ia) below:

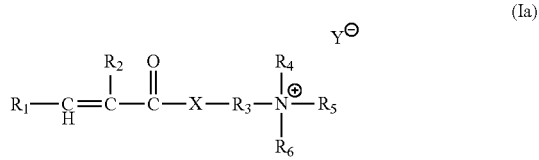

(Ia)

wherein:
  $R_1$ is chosen from hydrogen or methyl;
  $R_2$ is chosen hydrogen, or $C_1$-$C_4$ alkyl;
  $R_3$ is chosen $C_1$-$C_4$ alkylene;
  $R_4$, $R_5$, and $R_6$ are each independently chosen from hydrogen, or $C_1$-$C_4$ alkyl;
  X is chosen from —O—, or —NH—, preferably —O—; and
  Y is chosen from Cl, Br, I, hydrogensulfate or methosulfate;
  and mixtures thereof;
  b) said hueing dye is selected from the group consisting of small molecule dyes, polymeric dyes, dye-clay conjugates, and organic and inorganic pigments, in one aspect, said hueing dye comprises a chromophore selected from one or more of the following: acridine, anthraquinone, azine, azo, azulene, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof; and
  c) said additional perfume delivery comprises a material selected from the group consisting of a second microcapsule, a polymer assisted delivery system; a molecule-assisted delivery system; a fiber-assisted delivery system; a cyclodextrin delivery system; a starch encapsulated accord; and/or an inorganic carrier delivery system,
is disclosed.

U. A composition according to any of Paragraphs A, B, and N through T, having a viscosity of from 1 to 1500 centipoises (1-1500 mPa*s), from 100 to 1000 centipoises (100-1000 mPa*s), or from 200 to 500 centipoises (200-500 mPa*s) at 20 s$^{-1}$ and 21° C., is disclosed.

V. Use of a polymer having a surface energy of from about 20 to about 90, preferably from about 20 to about 75, more preferably from about 20 to about 50 to produce self-assembled particles in a liquid having a free water level from about 0.1% to about 90%, preferably from 0.2% to about 80%, more preferably 2% to about 70%, most preferably from about 5% to about 65%, preferably said composition comprises, based on total composition weight from about 0.1% to about 25%, preferably from about 0.5% to about 20% of a surfactant, preferably said surfactant comprises a nonionic surfactant, more preferably said surfactant comprises 5% to about 25% of said nonionic surfactant, preferably said surfactant comprises an anionic surfactant and a nonionic; or a water binding agent, is disclosed.

Graft Co-polymer

A graft copolymer molecule consists of a polymeric main chain, constituted of a long sequence of one monomer (the backbone), on which one or more polymeric side chains, constituted of monomers of a different chemical nature than the backbone, are attached. In graft copolymers a large number of parameters can be varied: the chemical nature, the molecular weight and the molecular weight distribution (MWD) of both the backbone and of the grafts, and the graft density along the backbone. Therefore, graft copolymers represent materials combining the properties of two or more polymers in one entity. Provided appropriate polymerization methods are used, tailor-made graft copolymers can be obtained. In common graft copolymers, the branches are randomly distributed along the backbone. The backbone and the branches may be homo- or copolymers but they differ in chemical nature or composition. Under the synthetic conditions used herein, the graft copolymer will also contain low levels of backbone homopolymer and side-chain graft homopolymer in addition to the graft copolymer itself.

By varying the nature and ratio's of the polymers used in the backbone and in the graft, it is possible to obtain graft co-polymers of different amphiphilicity. Suitable graft copolymers according to the invention are constituted of few long Poly Vinyl Acetate (PVAc) hanging off a Polyethylene (PEG) backbone. The graft co-polymer normally has only few graft points (only 1-3 PVAc grafts per the whole PEG chain, where the PEG chain is about 140 units long) with long PVAc chains.

Water Binding Agents

A water binding agent can be added to a liquid composition to lower its free water content. The water binding agents comprise organic acids, salts of organic acids, humectants, desiccants, natural sugar substitutes, artificial sugar substitutes, hydrogels and/or mixtures thereof.

Organic acids and salts thereof can be selected but not limited from the group consisting of citric acid, maleic acid, fumaric acid, salts thereof or mixtures thereof, preferably citric acid or salts thereof.

Humectants can be selected but not limited from the group consisting of 1,2,6-hexanetriol, butylene glycol, dipropylene glycol, glycerin, hexylene, glycol, panthenol, phytantriol, propylene glycol, sorbitol, triethylene glycol, polyglyceryl sorbitol, glucose, fructose, polydextrose, urea, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50).

Desiccants can be selected but not limited from the group consisting of activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium chlorate, sodium chloride, sodium hydroxide, sodium sulfate, sucrose.

Natural sugar substitutes can be selected but not limited from the group consisting of brazzein, curculin, erythritol, glycyrrhizin, glycerol, hydrogenated starch hydrolysates, inulin, isomalt, lactitol, luo han guo, mabinlin, maltitol, mannitol, miraculin, monatin, *sclerochiton ilicifolius*, monellin berries, osladin, pentadin, sorbitol, *stevia*, tagatose, thaumatin, xylitol.

Artificial sugar substitutes can be selected but not limited from the group consisting of aspartame, salts of aspartame, cyclamate, dulcin, glucin, neohesperidin dihydrochalcone, saccharin, sucralose.

Hydrogels can be selected but not limited from the group consisting of hydrogel forming polymers like silicone hydrogels, polyacrylamides, cross-linked polymers, polyethylene oxide, polyvinylpyrrolidone, polyvinyl alcohol, sodium polyacrylate, acrylate, or agarose, methylcellulose, hyaluronan, and other naturally derived polymers.

Benefit Agent

Suitable benefit agents include those selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti-skin aging agents, facial contrast agents, anti-dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents and mixtures thereof.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, DNases and amylases, or mixtures thereof. A typical combination may be a cocktail of conventional applicable enzymes like protease, lipase, cutinase and/or cellulase in conjunction with amylase.

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable peroxygen sources include peroxy acids. Typical monoperoxy acids useful herein include alkyl and aryl peroxyacids such as: (i) peroxybenzoic acid and ring-substituted peroxybenzoic acid, e. g. peroxy-α naphthoic acid, monoperoxyphthalic acid (magnesium salt hexahydrate), and o-carboxybenzamidoperoxyhexanoic acid (sodium salt); (ii) aliphatic, substituted aliphatic and arylalkyl monoperoxy acids, e. g. peroxylauric acid, peroxystearic acid, N-nonanoylaminoperoxycaproic acid (NAPCA), N, N-(3-octylsuccinoyl) aminoperoxycaproic acid (SAPA) and N, N-phthaloylaminoperoxycaproic acid (PAP); (iii) amidoperoxyacids, e. g. mononylamide of either peroxysuccinic acid (NAPSA) or of peroxyadipic acid (NAPAA). Typical diperoxyacids useful herein include alkyl diperoxyacids and aryldiperoxyacids, such as: (iv) 1,12-diperoxydodecanedioic acid; (v) 1,9-diperoxyazelaic acid; (vi) diperoxybrassylic acid; diperoxysebacic acid and diperoxyisophthalic acid; (vii) 2-decyldiperoxybutane-1, 4-dioic acid; (viii) 4,4'-sulfonylbisperoxybenzoic acid. Suitable bleach activators include perhydrolyzable esters and perhydrolyzable imides such as, tetraacetyl ethylene diamine, octanoylcaprolactam, benzoyloxybenzenesulphonate, nonanoyloxybenzene¬ sulphonate, benzoylvalerolactam, dodecanoyloxybenzenesulphonate. Other bleaching agents include metal complexes of transitional metals with ligands of defined stability constants.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In one aspect, the organosilicone may comprise a cyclic silicone. The cyclic silicone may comprise a cyclomethicone of the formula $[(CH_3)_2SiO]$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume—The perfume component may comprise a component selected from the group consisting of:
(1) a free perfume
(2) a perfume delivery technology;
(3) a pro-perfume;
(4) a low odor detection threshold perfume ingredients, wherein said low odor detection threshold perfume ingredients may comprise less than about 25%, by weight of the total neat perfume composition; and
(5) mixtures thereof.

In one aspect the following perfume delivery technologies (PDTs) may be used.

Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

Matrix Systems: The fragrance is dissolved or dispersed in a polymer matrix or particle. Absorption and/or adsorption into or onto polymeric particles, films, solutions, and the like are aspects of this technology. Nano- or microparticles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephLhalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, aminoplast, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2

Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines.

Cyclodextrin (CD): This technology approach uses a cyclic Starch Encapsulated Accord (SEA.

Zeolite & Inorganic Carrier (ZIC): This technology relates to the use of porous zeolites or other inorganic materials to deliver perfumes.

Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiff bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester.

Fabric Hueing Agents—The composition may comprise a fabric hueing agent (sometimes referred to as shading, blueing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive (or hydrolysed forms thereof), Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes as disclosed in U.S. Pat. No. 8,268,016 B2, or dyes as disclosed in U.S. Pat. No. 7,208,459 B2, or dyes disclosed in U.S. Pat. No. 8,247,364 B2 and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113, fabric hueing agents that undergo a transition on storage or during or after use that either (1) changes the extinction coefficient in the visible range at a set wavelength (400-750 nm) from less than 1000 $M^{-1}cm^{-1}$ to one greater than 5,000, preferably greater than 10,000, more preferably greater than 20,000, even more preferably greater than 50,000, most preferably greater than 80,000 or even 100,000 $M^{-1}cm^{-1}$, (2) increases the extinction coefficient in the visible range at a set wavelength (400-750 nm) by a factor of at least five, preferably ten or even twenty fold wherein the final extinction coefficient at the set wavelength is at least 10,000 $M^{-1}cm^{-1}$, or (3) shifts the wavelength of the maximum extinction coefficient within the visible range from the pre-transition value by at least 25 nm, preferably 50 nm, even more preferably 75 nm, most preferably by 100 nm or more, wherein the final wavelength of the maximum extinction coefficient within the visible range is from about 550 to 700 nm, preferably from 550 to 650 nm, and/or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through I 1, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green GI C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green GI C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green GI C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

In one aspect, materials suitable for incorporation into the benefit agent containing delivery particles of the present invention include leuco dyes, antioxidants, and mixtures thereof. Leuco dyes are known in the prior art to exhibit a change from a colorless or slightly colored state to a colored state upon exposure to specific chemical or physical triggers. The chemical or physical triggers that bring about the coloration change include, but are not limited to, oxidation, intramolecular ring opening, pH change, and exposure to heat and/or cold or light (e.g. UV light). Preferred Leuco dyes include those that develop a color upon triggering that is suitable for use as a shading dye to increase whiteness perception. Triarylmethane compounds are a class of leuco dyes useful in one aspect.

The aforementioned fabric hueing agents can be used in combination (any mixture of fabric hueing agents can be used).

Adjunct Materials

The disclosed compositions may include additional adjunct ingredients that are in addition to the materials found in the benefit agent delivery particles. Such adjunct ingredients may include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, scavengers and/or pigments. Other embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

Surfactants—Surfactants utilized can be of the anionic, nonionic, zwitterionic, ampholytic or cationic type or can comprise compatible mixtures of these types. Anionic and nonionic surfactants are typically employed if the fabric care product is a laundry detergent. On the other hand, cationic surfactants are typically employed if the fabric care product is a fabric softener. In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. In one embodiment, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines, imidazoline quat materials and quaternary ammonium surfactants, preferably N, N-bis (stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; 1, 2 di (stearoyl-oxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants—The compositions may contain from about 0.1%, to about 10%, by weight of dispersants. Suitable dispersants are water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, DNases and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-sulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Other examples of suitable stabilizers may include hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In one aspect, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume—The perfume component may comprise a component selected from the group consisting of:
 (1) a free perfume
 (2) a perfume capsule, or a moisture-activated perfume capsule, comprising a perfume carrier and an encapsulated perfume composition, wherein said perfume carrier may be selected from the group consisting of cyclodextrins, starch capsules, porous carrier capsules, and mixtures thereof; and wherein said encapsulated perfume composition may comprise low volatile perfume ingredients, high volatile perfume ingredients, and mixtures thereof;
 (3) a pro-perfume;
 (4) a low odor detection threshold perfume ingredients, wherein said low odor detection threshold perfume ingredients may comprise less than about 25%, by weight of the total neat perfume composition; and
 (6) mixtures thereof; and Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive (or hydrolysed forms thereof), Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes as disclosed in U.S. Pat. No. 8,268,016 B2, or dyes as disclosed in U.S. Pat. No. 7,208,459 B2, or dyes disclosed in U.S. Pat. No. 8,247,364 B2 and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113, fabric hueing agents that undergo a transition on storage or during or after use that either (1) changes the extinction coefficient in the visible range at a set wavelength (400-750 nm) from less than 1000 $M^{-1}cm^{-1}$ to one greater than 5,000, preferably greater than 10,000, more preferably greater than 20,000, even more preferably greater than 50,000, most preferably greater than 80,000 or even 100,000 $M^{-1}cm^{-1}$, (2) increases the extinction coefficient in the visible range at a set wavelength (400-750 nm) by a factor of at least five, preferably ten or even twenty fold wherein the final extinction coefficient at the set wavelength is at least 10,000 $M^{-1}cm^{-1}$, or (3) shifts the wavelength of the maximum extinction coefficient within the visible range from the pre-transition value by at least 25 nm, preferably 50 nm, even more preferably 75 nm, most preferably by 100 nm or more, wherein the final wavelength of the maximum extinction coefficient within the visible range is from about 550 to 700 nm, preferably from 550 to 650 nm, and/or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green GI C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green GI C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green GI C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

The aforementioned fabric hueing agents can be used in combination (any mixture of fabric hueing agents can be used).

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Method of Use and Treated Situs

Compositions containing the benefit agent delivery particle disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed In one aspect, a method of treating and/or cleaning a situs, said method comprising
   a) optionally washing, rinsing and/or drying said situs;
   b) contacting said situs with a composition according to the invention;
   c) optionally washing and/or rinsing said situs; and
   d) optionally dried by drying passively and/or via an active methods such as a laundry dryer.

For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

In one aspect, a situs treated with any embodiment of any composition disclosed herein is disclosed.

Test Methods

It is understood that the test methods that are disclosed in the Test Methods Section of the present application should be used to determine the respective values of the parameters of Applicants' invention as such invention is described and claimed herein.

1. Hydrodynamic Diameter of Particles Test Method

This method is used to determine the intensity-averaged hydrodynamic diameter of particles via Dynamic Light Scattering (DLS). The DLS apparatus comprises a model 9000 AT correlator and a model 200 SM goniometer, plus accompanying Dynamic Light Scattering Software (vers. 5.78) (all from Brookhaven Instruments, USA), or equivalents. The system is equipped with temperature thermostat, and an EMI 9863B/350 photomultiplier, or equivalent and a Coherent DPY315M-100 Nd:YAG laser ($\lambda$=532 nm) which is linearly polarized in the vertical direction. The thermostat is set to 25° C. Click on "Control", then "Motor", then "Set Angle" and select 900. Set the Pinhole to 100 and open the correlator shutter to the laser position (532). Place 1.5 ml of sample into a test tube tube (such as 12×75 mm Disposable Borosilicate Glass Test Tube) and centrifuge the tube and sample at 4000 rpm for 5 minutes. Put the test containing the test sample into the DLS instrument. In the Software click on "Correlation Functions", then "New Window", and then click "OK". A "Correlator Control Window" appears, press on Start (green button) and check the Average Count Rate (A CR). If A CR>500 kcps stop the measurement and dilute the sample and repeat until an A CR value less than 500 kcps is obtained. Click on "Graphs", then "Correlation Functions", and then "New Window". Click on "ISDA", then on "Cumulant Analysis", and then on "New Window". In the "Correlator Control Window" click on "Params" and add the sample parameters; including: select water as Liquid; select 90 at Angle' enter 532 at Wavelength; Flag "Use dust filter". In the "Correlator Control Window" click on "Dur", then on "Elapsed time" and select 2 minutes. In the "Correlator Control Window" click on "Layout" and optimize the first and last delay depending on the autocorrelation curve. In the "Correlator Control Window" press Start and wait until the measurement is completed. The intensity-averaged Hydrodynamic Diameter value is reported in the "Cumulant Analysis" window, and is reported in units of nanometers.

2. Surface Energy Test Method

Total Surface Energy values (in units of mJ/m$^2$), are determined by conducting contact angles measurements on polymer test samples in accordance with the standard method ASTM D7490-13 Standard Test Method for Measurement of the Surface Tension of Solid Coatings, Substrates and Pigments using Contact Angle Measurements, with modifications as specified below. The polymer test sample is analyzed when prepared as a surface-coating test substrate. This polymer test substrate coating is prepared by spreading a neat polymer test sample onto a glass slide and drying so that a flat bulk coating of polymer is created on the glass slide.

Reference measurements are conducted by measuring the contact angles on both sides of drops of distilled water and diiodomethane (all available from Sigma Aldrich, St. Louis, Mo.) placed on the gloss-finished side of the clean untreated ceramic tile. The two values are then substituted into two separate expressions of the Owens-Wendt-Kaelble equation (one for each liquid). This results in three equations and two unknowns, which are then solved for the dispersion and polar components of surface tension. A Goniometer instrument is required, such as the Model 200 (from First Ten Angstroms Inc, Portsmouth, Va. USA) or equivalent, and comprises a controlled light source, a stage to hold the tile, and a microscope or camera for viewing of the drop on the tile. A gas—tight syringe, such as a 1 mL hypodermic equipped with a No. 27 blunt tipped stainless steel needle, and capable of providing 100 to 200 drops from 1 mL. Type II reagent water (distilled) in accordance with ASTM Specification D1193-99, is required, as is Diiodomethane (99+% purity). The tile should not be touched with fingers or contaminated in any way, during or before the testing or during positioning on goniometer stage. Testing is conducted while the tile is mounted in the goniometer within a constant temperature (73±2° F.) and constant humidity environment (50±10% RH). Set up the goniometer and level the stage according to the manufacturer's instructions. Measure contact angles of each droplet of water and diiodomethane on the tile as described in ASTM D7334 or the manufacturer's literature for the instrument being used. Position the tile to deposit a drop without visible distortion of the drop shape due to movement. Set the tip of the hypodermic needle at the distance from the surface recommended by the manufacturer of the instrument (3 mm [⅛ inches]) and deposit a drop of test liquid 5 μL in size on the tile. Drop size should be controlled to ±0.1 μL. Focus the camera or video device so that the image of the drop can be captured. Two angle measurements are made (one on each drop edge), on each of two drops on the tile using, commercial software designed to extract contact angles from movies or images (e.g., First Ten Angstroms Inc., software version 2.1, build 363, or equivalent). If the contact angles on two edges are different by more than 4°, the values are discarded and the test is repeated. This measurement is replicated 6 times, on new droplets each time. The contact angle for the tile shall be the average of the twelve angles measured on the six droplets. The Owens-Wendt-Kaelble equation:

$$\sigma_{lg}^T \frac{(\cos\theta + 1)}{2} = (\sigma_{lg}^D \gamma_{sg}^D)^{1/2} + (\sigma_{lg}^P \gamma_{sg}^P)^{1/2}$$

where:
   $\theta$=the average contact angle for the test liquid on the test substrate, $\sigma_{lg}^T$=the total surface tension of the test liquid in dyn/cm $\sigma^D$ and $\sigma^P$=the dispersion and polar components of the liquid surface tension, respectively, also in dyn/cm.

$\sigma_{sg}$=the total surface energy of the test substrate in dyn/cm $\sigma^D$ and $\sigma^P$=the dispersion and polar components of the test substrate, respectively, also in dyn/cm.

| Solvent | Surface Tension($\sigma_{lg}$) (dyn/cm) | | |
|---|---|---|---|
| | Nonpolar | Polar | Total |
| Diiodomethane | 50.8 | 0 | 50.8 |
| Water | 51.0 | 21.8 | 72.8 |

The Owens-Wendt-Kaelble equation is simplified to the following when a dispersive (nonpolar) solvent such as diiodomethane is used:

$$\sigma_{lg}^T \frac{(\cos\theta + 1)}{2} = (\sigma_{lg}^D \gamma_{sg}^D)^{1/2}$$

The dispersive (nonpolar) component of surface energy ($\sigma_{sg}^D$) is determined. Surface tension properties for diiodomethane are known and included in the table above. The contact angle is experimentally determined using the method delineated above. Upon inserting the calculated dispersive component of surface energy ($\sigma_{sg}^D$) for the substrate into the Owens-Wendt-Kaelble equation delineated above and using the contact angles determined for water, the polar component of surface energy ($\sigma_{sg}^P$) of the test substrate is determined using the known surface tension properties for water (included in the table above). The dispersive component ($\sigma_{sg}^D$) of the test substrate is determined with diiodomethane as explained above.

The surface energy value reported for the polymer test sample (as the bulk polymer coating test substrate), is the Total Surface Energy expressed in units of mJ/m².

3. Particle Diameter and Structure Test Method

Microscopy is used to measure the number-weighted average diameter of the co-polymer particles. Microscopy is also used to determine the structure of the particles via observing the frequency and the location of benefit agent regions in the particles. The microscopic measurement particle diameter may be conducted using any microscopic technique capable of imaging the external size of the particles in the sample. The microscopic determination of structure may be conducted using any microscopic technique capable of imaging the internal presence and location of the benefit agent regions in the particles. Suitable microscopy techniques may include but are not limited to: Scanning Electron Microscopy (SEM); Phase Contrast Microscopy; Differential Interference Contrast microsopy (DIC); Fluorescence Microscopy; and Confocal Laser Scanning Fluorescence Microscopy (CLSM). One of skill will understand that different and various sample preparation steps may be required for the different imaging techniques which may be suitable. In all cases, the number-weighted average diameter of the particles is calculated from the values obtained by microscopically observing and measuring the diameter of at least 30 randomly selected particles in a sample.

The structure of the particles is assessed by microscopically observing and determining the frequencies and locations of all observable benefit agent regions in at least 30 randomly selected particles in a sample. In the case of optical light microscopy techniques it is suitable to use a high magnification water-immersion objective lens such as a 63×/1.2 NA Water lens (Zeiss) to observe 0.5 mL of sample placed into a Chambered Coverglass such as Chambered #1.0 Borosilicate Coverglass System (such as from LabTek) and to dilute the sample as necessary to obtain unobstructed images of the particle diameter and structure. In the case of fluorescence microscopy and especially fluorescence confocal laser scanning microsopy (CLSM), the selective labeling of the polymers and the benefit agents with different fluorescent dyes can enable their separate detection via excitation with different wavelengths of light. For example, by labeling the polymer(s) with a red dye label such as Rhodamine isothiocyanate ($\lambda$ex=561 nm), and the benefit agents with a dye probe having a different excitation wavelength, for example such as Coumarin 6 ($\lambda$ex=488 nm), it is then possible to determine where the polymer and the benefit agents are located by means of different filters and detectors on the microscope. By using the overlay of images from the different detectors it is possible to identify the regions of co-localization, and observe the frequency and spatial location of the benefit agent regions relative to the particle and its polymer regions.

In the examples, an amphiphilic polymer has been labeled with Rhodamine isothiocyanate $\lambda$ex=561 nm and imaged via Confocal Laser Scanning Fluorescence Microscopy. This method permits easy observation and determination of the structure of the particles. Three different kinds of microcapsule particle structure are shown in the Figures: Matrix like capsules where the polymer is located also within the core; Core-shell capsules where the polymer forms a wall around the core; and Multiple-core capsules.

4. Self-Assembly Index Test Method

With this method one can separate particles in the Micro scale and Macro scale (from 1 μm to 1 cm) from particles in the sub-Micro scale (<1 μm). For polymers able to self-assemble in a specific solvent, the Self-Assembly Index (SAI) is defined as:

$$SAI = \frac{w_{SA}}{w_{free} + w_{SA}} * 100$$

where $w_{SA}$ is the weight fraction of the self-assembled polymer, and w is the weight fraction of the free polymer.

Materials:
- Balance with accuracy of ±0.0001 g (such as Sartorius CP225D).
- Magnetic stirrer-(such as MST VELP Scientifica, Italy) and stir bar
- Dialysis tubing cellulose membrane (cut-off 14.4 kDa, D9777-100FT, Sigma-Aldrich, USA, or equivalent) and 100 ml Beaker.
- UV/Vis Spectrometer-Lambda 900 (Perkin Elmer) and UV/Vis Spectrometer Software-Spectrum (PerkinElmer), or equivalents.
- Disposable cuvettes (such as 1.5 ml semimicro, Brand, Cat. No. 7591 50, dimensions 12.5×12.5×45 mm).

Note that the total amount of polymer in the detergent formulation ($w_{TOT}=w_{SA}+w_{free}$) must be known to calculate the SAI.

About 1 g of detergent formulation containing a labeled polymer is placed inside a dialysis membrane and weighted on the balance (take note of the weight). Seal the membrane at both ends. Weigh about 50 g of detergent formulation inside the beaker (take note of the weight). Insert the stir bar and the sample inside the beaker containing the formulation and place it on the magnetic stirrer. Keep at a constant stirring of 500 rpm for 72 hours (if necessary, cover the beaker with some plastic paraffin film, such as Parafilm or equivalent). After the dialysis, remove the membrane from the beaker and precisely weigh the remaining detergent formulation ($W_{form}$). After the dialysis, take 1.5 g of the external matrix and place in a cuvette. This will be referred as "sample". Take 1.5 g of non-dialyzed detergent formulation and place in a cuvette. This will be referred as "blank".

Turn on the UV/Vis spectrometer and control software
Insert the blank sample in the sample location inside the instrument
Click on "Autozero" and wait until the procedure is completed
Click on the tab "Utilities" and then on "Configuration . . . "
Generate directories for both Methods and Data and then press "Ok"
In the scan panel choose nm for abscissa mode; 1 for number of cycles; 800 for abscissa start; and 400 for abscissa end
In the sample panel insert 1 in number of samples
Replace the blank with the sample in the instrument's sample location
Press "Start" and wait until the spectrum is collected
A peak relative to the absorption of the polymer labeled molecule should appear. Take note of the Absorbance value at the maximum lambda of absorption.

Calibration curve and results—Prepare at least 4 samples at different concentration of labeled polymer in the detergent formulation. These will be referred as "standards". Collect spectra for all standards as described.

Take note of the Absorbance value at the maximum of the absorption peak in the spectra
Plot Absorbance values vs concentration. According to Beer's law, a linear dependence should be obtained
Use the calibration curve to determine sample concentration (from Absorbance data). This concentration represents the amount of free polymer in 1.5 g of external matrix
Scale to the total amount of external matrix ($W_{form}$) to obtain $w_{free}$.
Calculate $w_{SA} = w_{TOT} - w_{free}$.
Calculate SAI according to the equation provided.

5. Free Water Content Test Method

Free water content (FWC) refers to the amount of freezable non-bound water with a temperature of fusion around 0° C. and is defined as:

$$FWC \% = \left(\frac{\Delta H_{f,sample} * m_{sample}}{\Delta H_{f,H_2O}}\right) / m_{sample} * 100$$

where $\Delta H_{f,sample}$ is the enthalpy of fusion of water in the sample in J/g, $m_{sample}$ is the weight of the sample in g, and $\Delta H_{f,H_2O}$ is the enthalpy of fusion of pure water in J/g.

1. Materials

Differential scanning calorimetry with refrigerated cooling system, such as DSC-Q2000 with DSC software Advantage for Q series version 5.4.0, and Analysis software such as Universal analysis 2000 version 4.5A (TA instruments), or equivalents.

Analytical balance (sensitivity 0.0001 g), such as Sartorius CP225D.

DSC Steel pan, such as Perkin Elmer model: 0319-1525 (bottom) 0319-1526(cover) 0319-1535(O-ring)

2. Procedure to Measure $\Delta H_{f,sample}$

1) Weight on the balance the Steel pan with its cover and the O-ring. Note the weight ($W_p$)
2) Assemble the O-ring with the cover
3) Weight on the balance the amount of sample (10-20 mg) added into the pan, note the weight ($W_{s+p}$)
4) Close the pan hermetically
5) Calculate $W_s = W_{s+p} - W_p$
6) Insert the pan in the DSC
7) Open the Nitrogen line (flow must be not below 50 ml/min)
8) Open the software TA instrument explorer
9) Turn on the cooler from the button control and then press "event on" on the software
10) The software is subdivided into three main parts. (Summary-procedure-notes). In summary you have to write the details of the sample (sample name, $W_p$, $W_s$) and the type of pan you are using, then select the directory to save the data and flag "pan mass". In the 'Procedure' panel by pressing 'Editor' you can write down the procedure needed for your samples. Here we report the procedure used to calculate the FWC.

Equilibrate at 5° C.
Data storage on
Ramp 0.5°/min to −80° C.
Mark the end of the cycle "0"
Ramp 0.5° C./min to 25° C.
Mark the end of the cycle "1"

In the 'notes' panel choose the appropriate calibration in this case (Steel pan 0.5° C./min)

11) Press 'apply' button to complete the run procedure and start from the main software panel.
12) Once the run is done it will be green flagged 3. Procedure to Analyze the Data 1) Open the data collected with the DSC, using the analysis software (Universal analysis 2000 version 4.5A)
2) Expand the region of interests (typically between −20 and +5° C.)
3) Click on "Integrate Peak Linear"
4) Double-click before and after the thermal peak to insert two cursors that determine the integration limits
5) Right-click in between the two cursors and click on "accept limits"
6) The software calculates $\Delta H_{f,sample}$ in J/g 4. Determination of $\Delta H_{f,H2O}$ Instead of using the standard value of 333.55 J/g as $\Delta H_{f,H2O}$, one can calculate $\Delta H_{f,H2O}$ for the instrument used (the value should be comprised between 333.55±30 J/g).

Three samples of 1-2 mg of deionized water (such as MilliQ grade, 18.2 MΩ cm) each are precisely weighted in a DSC steel pan (take note of the precise weight) and placed in a DSC. All samples are analyzed using the same procedure used to determine $\Delta H_{f,sample}$. Once determined $\Delta H_{f,sample}$, $\Delta H_{f,H2O}$, one can calculate the FWC.

6. SAXS Index Test Method

For polymers able to self-assemble in a specific solvent, the SAXS Index (SAXS) is defined as:

$$SAX = \frac{w_{SA}}{w_{free} + w_{SA}} * 100$$

where $w_{SA}$ is the weight fraction of the self-assembled polymer, and $w_{free}$ is the weight fraction of the free polymer.

1. Background

Small angle X-ray scattering (SAXS) allows for the determination of the structures of materials whose dimension ranges between 1 to about 100 nm, depending on the instrument setup.

In a SAXS experiment, the scattering intensity for particles in solution is reported to be:

$$\frac{d\sum(Q)}{d\Omega} = I(Q) = (N/V)V_p^2 \Delta\rho^2 P(Q) S(Q)$$

where N/V is the number density of particles per cm$^3$, $V_p$ is the particle volume, $\Delta\rho^2$ is the contrast factor, P(Q) is the single particle form factor, and S(Q) is the inter-particle structure factor. In diluted conditions the inter-particle interactions are negligible, so S(Q)=1. Q is the scattering vector and is equal to:

$$Q = (4\pi/\lambda)\sin(\theta/2)$$

where $\lambda$ is the X-ray wavelength and $\theta$ is the scattering angle.

When the intensity is in the absolute scale, and if self-assembled polymeric structures are larger than 100 nm, by fitting the experimental curves with the proper form factor one can obtain the number density of scattering particles that is the weight fraction of the free polymer ($w_{free}$).

If the total amount of the polymer ($w_{tot}$) is known, then:

$$w_{SA} = w_{tot} - w_{free}$$

2. Contrast Factor

The contrast factor $\Delta\rho^2$ can be obtained as the difference between the scattering length density of the polymer ($\rho_{pol}$) and the solvent ($\rho_{solv}$).

The scattering length density can be calculated in two ways:

1) Using the formula:

$$\rho = \Sigma z_i r_e / V_{mol}$$

where $z_i$ is the total number of electrons of the molecule, $r_e$ is the electron radius (2.81*10$^{-13}$ cm) and $V_{mol}$ is the molecule volume that can be obtained by the relation:

$$V_{mol} = \frac{M_W}{dN_a}$$

where $M_w$ is the molecular weight of the molecule, d is the density of the material, and $N_a$ is the Avogadro's number.

2) Inserting the chemical formula and the density of the material in the "Neutron activation and scattering calculator" software available at https://www.ncnr.nist.gov/resources/activation.

In the case of, for example, a copolymer AB with 40% of block A and 60% of block B, the scattering length density can be calculated as:

$$\rho_{AB} = \rho_A * 0.4 + \rho_B * 0.6$$

3. Form Factor

For analysis of SAXS data, Wavemetric's software Igor Pro 6.2 (or higher) (https://www.wavemetrics.com/products/igorpro/igorpro.htm) or SasView software (http://www.sasview.org/) to be installed on a PC or Mac are mandatory. Form factors for SAXS curve fittings are available as a downloadable package at https://www.ncnr.nist.gov/programs/sans/data/red_anal.html .zip format (NCNR_SANS_package.zip, Current Release v7.41—June 2016).

Unzip this file, open it with Igor Pro or SasView and follow the instructions for package installation. Once the installation is done, in order to load all the form factors, one has to:

Open Igor Pro software

Go to the "Macros" tab and select "Load NCNR Analysis Macros"

Select the desired form factor in the "Procedure List" window and click "Include File(s)"

In the "Curve Fit Setup" window select the desired procedure and then click "Plot 1D Function"

In the pop-up window "Plot*selected procedure*" enter the desired number of data points for model, the minimum and the maximum Q values for model (in Å$^{-1}$)

Click on "Continue" and a form factor with default values is now generated.

4. SAXS Data Correction

Once collected the SAXS curve for a sample, the Intensity must be corrected in the form:

$$I_s(Q) = \frac{(I_{s+c}(Q) - I_b)}{T_{s+c}} - \frac{(I_c(Q) - I_b)}{T_c}$$

where $I_s(Q)$ is the subtracted and rescaled scattering intensity, $I_{s+c}(Q)$ is the original intensity obtained from the instrument, $I_c(Q)$ is the scattering of empty cell and solvent, $I_b$ is the scattering with beam blocked, and $T_{c+s}$ and $T_c$ are the original sample and empty cell with solvent transmissions, respectively. Using the beam counts $I_0(\lambda)$ the scattering intensity is scaled to an absolute cross section (units in cm$^{-1}$) as:

$$\frac{d\sum(Q)}{d\Omega} = \frac{I_s(Q)}{I_0(\lambda) T d \Delta\Omega}$$

where T is the sample transmission, d is the sample thickness and $\Delta\Omega$ is the solid angle subtending one detector cell. The 2D corrected and scaled data are radially corrected to produce 1D data, generally with in-house software from the SAXS facility.

5. SAXS Data Analysis

In Igor Pro (or SasView) software, load the Intensity, Q, and error data collected from the experiment and plot a Log(Intensity) vs Log(Q) graph. The sample curve, expressed as Log(Intensity) vs Log(Q), is assessed. A curve which has a constant intensity for at least 10 points in the low-Q region is considered acceptable and is used in subsequent calculations, otherwise SAXS index cannot be calculated. After loading the desired form factor and generating the coefficient wave as reported in section 4, one must follow this methodology:

Go to the "Analysis" tab and select "Curve Fitting . . . "
In the "Function and Data" panel select the fitting function, the Y Data and the X Data
In the "Data Options" panel select the error wave under "Weighting"
In the "Coefficients" panel select the coefficient wave, insert the correct values for contrast and click "Do it"

After the fitting procedure is completed, the fitting coefficients including the Volume fraction are printed. The volume fraction represents the volume occupied by the polymer divided the total volume. By means of the density one con obtain the weight fraction and so calculate the SAXS.

7. Dissolution Index Test Method

Capsule particle formation is strongly influenced by the free water content. By dilution with water, the free water content of a sample is increased and when it becomes higher than the critical value, a complete dissolution of the capsule particles occurs. Dissolution upon dilution is indicative of self-assembled systems. The test method to determine the Dissolution Index value of a test sample is conducted in an environment that is at 25° C.

1) Measure the free water content of the sample (i.e., FWCsample) by DSC using the Free Water Content Test Method specified herein.
2) Add 0.5 ml of the test sample into a chambered coverglass and observe the microcapsules using an optical microscope.
3) Prepare dilutions of the test sample by adding aliquots of deionized water to 0.5 ml of original sample, (e.g., dilution A=original sample+0.1 ml water, dilution B=original sample+0.2 ml water, etc.)
4) Check the diluted samples under the microscope and determine which sample is the least diluted sample in which the capsules have dissolved (i.e. are not visible anymore). Discard all other dilutions.
5) Measure the free water content of the remaining diluted sample in which the microcapsules had dissolved (i.e. FWCdil), using the Free Water Content Test Method specified herein.
6) If FWCdil−FWCsample is less than 60%, the sample has a Dissolution Index of 1. If the FWCdil−FWCsample is equal to or greater than 60%, the sample has a Dissolution Index of 0.

8. Weight-Average Molecular Weight Test Method

Weight-average molecular weight values are determined using high performance liquid chromatography (HPLC) instrument system with a refractive index detector, such as the Waters Alliance 2695 system equipped with autosampler and Waters 2414 refractive index detector (Waters Inc., Milford, Mass., USA). Data storage and analysis are performed with Astra 6.1.6 software (Wyatt Technologies, Santa Barbara, Calif., USA). The chromatographic conditions used are as specified in the table below:

| Parameter | Conditions |
| --- | --- |
| Column Set | Guard Column - TSK Gel Guard HXL-H in-line with Three TOSOH columns: TSK Gel G4000HXL Catalog #0016137; TSK Gel G5000HXL Catalog #0016138; TSK Gel G6000HXL Catalog #0016139; |
| Mobile Phase | Tetrahydrofuran (THF) |
| Flow Rate | 1 mL/min |
| Column Temperature | 25° C. |
| Injection Volume | 100 μL |
| Detector Temperature | 35° C. |

In carrying out the calculations, the results are calibrated using a set of 12 polystyrene reference samples, such as the EasiVial PS-M set (Agilent Technologies, Santa Clara, Calif.) having known molecular weights ranging from 162 to 364,000 $M_p$ and using a second order fit. The molecular weight analyses are determined using a tetrahydrofuran (THF) mobile phase. The table below shows the molecular weights and the retention times of the polystyrene standards:

| Standard Number | Average Reported Mp | Retention Time (min) |
| --- | --- | --- |
| 1 | 364,000 | 21.75 |
| 2 | 195,300 | 23.02 |
| 3 | 110,500 | 24.18 |
| 4 | 49,010 | 25.78 |
| 5 | 30,230 | 26.61 |
| 6 | 12,980 | 27.90 |
| 7 | 7,640 | 28.60 |
| 8 | 2,970 | 29.71 |
| 9 | 1,150 | 30.79 |
| 10 | 855 | 31.10 |
| 11 | 370 | 31.91 |
| 12 | 162 | 32.95 |

9. Grafting and Ratio of Polyalkylene Glycol: Vinyl Acetate Moieties Test Methods The percent grafting is determined by 13C-NMR using a Bruker 600 MHz NMR. An inverse-gated 30° pulse sequence was used, with 16,000 scans and relaxation delay of 5 sec. Samples are prepared at 50 mg/ml in deuterated DMSO-d6 with addition of 0.79 mg/ml $Gd(NO_3)_3$ and 0.31 mg/ml Inositol as a Paramagnetic Relaxation Reagent. The ratio of the integration of the area between 76.75-77.5 ppm for the graft methine carbon and the integration of the area between 70.00-70.65 ppm for the PEG carbons is calculated and converted to a percent.

The weight percents for Polyalkylene Glycol: Vinyl Acetate Moieties are calculated by averaging the integration of the area of the NMR proton spectra between 1.35-2.07 ppm & 4.65-5.1 ppm for polyvinyl acetate and 3.38-3.58 ppm for Polyalkylene Glycol. The integrations are divided to find a molar ratio, and then multiplied by their respective molar mass to calculate the weight percents.

10. Method of Measuring Viscosity:

Viscosity is measured using a HAAKE MARS from Thermo Scientific using a 60 mm 1° Cone and a gap size of 52 micrometers. The shear viscosity at 20 $s^{-1}$ can be obtained from a logarithmic shear rate sweep from 0.01 $s^{-1}$ to 1200 $s^{-1}$ at 21° C. The viscosity is expressed as centipoise (cP).

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Purification of Sokalan HP-22

Sokalan HP-22 (BASF) is a 22% solution of Poly(ethylene oxide-g-vinyl acetate) in water. To evaluate this material, the polymer solution is first placed into a 1000 MWCO dialysis tube (SpectaPor). The sample is then dialyzed against RO water with water flow held such that complete water replacement occurs every 2 hours for a total of 48 hours of dialysis. The sample is then lyophilized using a Labconco lyophilizer.

PEG-g-PVAc: General Synthetic Procedure (Examples 1-10)

(See Table 1 below for specific amounts)

A reaction vessel with stirrer and reflux condenser is charged with the initial PEG under a nitrogen atmosphere and melted at the reaction temperature. After addition of the initial charges of vinyl acetate (freshly distilled) and t-butyl peroxypivalate initiator (dissolved in the initial dipropylene glycol), the contents are stirred for 5 minutes. To the vessel, simultaneously with constant flow rate, is metered the vinyl acetate feed (freshly distilled) over 6 hours, and t-butyl peroxypivalate initiator feed 1 (dissolved in dipropylene glycol) over 7 hours. The internal temperature is maintained at the reaction temperature with stirring throughout. After initiator feed 1 is finished the mixture is stirred at the reaction temperature for 1 hour. Then at the reaction temperature, t-butyl peroxypivalate initiator feed 2 (dissolved in dipropylene glycol) is added. One hour later t-butyl peroxypivalate initiator feed 3 (dissolved in dipropylene glycol) is added. The reaction is stirred at the reaction temperature for 4 hours.

The reaction mixture is vacuum distilled at 90° C. to remove residual vinyl acetate.

TABLE 1

Reagent quantities-Examples 1-10

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Initial PEG charge (grams) | 22.1 | 22.5 | 22.5 | 22.5 | 64.17 | 64.17 | 64.17 | 64.17 | 22.5 | 22.5 |
| PEG Mw | 6000 | 6000 | 12000 | 12000 | 12000 | 12000 | 6000 | 6000 | 2000 | 2000 |
| Reaction Temperature, (° C.) | 70 | 90 | 70 | 90 | 70 | 90 | 70 | 90 | 70 | 90 |
| Initial vinyl acetate charge (grams) | 1.69 | 1.69 | 1.69 | 1.69 | 7.47 | 7.47 | 7.47 | 7.47 | 1.69 | 1.69 |
| Initial initiator charge (grams) | 0.02 | 0.02 | 0.02 | 0.02 | 0.058 | 0.058 | 0.058 | 0.058 | 0.02 | 0.02 |
| Initial dipropylene glycol charge (grams) | 0.061 | 0.061 | 0.061 | 0.061 | 0.174 | 0.174 | 0.174 | 0.174 | 0.061 | 0.061 |
| Vinyl acetate feed (grams) | 50 | 50 | 50 | 50 | 21.3 | 21.3 | 21.3 | 21.3 | 50 | 50 |
| Initiator feed 1 (grams) | 0.409 | 0.409 | 0.409 | 0.409 | 0.409 | 0.409 | 0.409 | 0.409 | 0.409 | 0.409 |
| Dipropylene glycol for initiator feed 1 (grams) | 1.23 | 1.23 | 1.23 | 1.23 | 1.23 | 1.23 | 1.23 | 1.23 | 1.23 | 1.23 |
| Initiator feed 2 (grams) | 0.475 | 0.475 | 0.475 | 0.475 | 0.475 | 0.475 | 0.475 | 0.475 | 0.475 | 0.475 |
| Dipropylene glycol for initiator feed 2 (grams) | 1.425 | 1.425 | 1.425 | 1.425 | 1.425 | 1.425 | 1.425 | 1.425 | 1.425 | 1.425 |
| Initiator feed 3 (grams) | 0.475 | 0.475 | 0.475 | 0.475 | 0.475 | 0.475 | 0.475 | 0.475 | 0.475 | 0.475 |
| Dipropylene glycol for initiator feed 3 (grams) | 1.425 | 1.425 | 1.425 | 1.425 | 1.425 | 1.425 | 1.425 | 1.425 | 1.425 | 1.425 |

TABLE 2

Polymer Characterization of Polymers 1-10

| Sample | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Mn (kDa) | 5.0 | 5.8 | 6.0 | 5.7 | 3.8 | 3.9 | 3.6 | 3.6 | 4.0 | 4.3 |
| Mp (kDa) | 12.0 | 11.9 | 20.5 | 22.4 | 6.5 | 6.3 | 6.3 | 6.0 | 6.9 | 6.5 |
| Mw (kDa) | 10.3 | 11.05 | 13.05 | 14.65 | 5.95 | 6.2 | 5.7 | 5.6 | 7.7 | 10.2 |
| PDI | 2.1 | 1.9 | 2.3 | 2.6 | 1.6 | 1.6 | 1.6 | 1.6 | 1.9 | 2.4 |
| wt % PEO | 29 | 31 | 34 | 30 | 70 | 72 | 72 | 79 | 30 | 30 |
| wt % PVAc | 71 | 69 | 66 | 70 | 30 | 28 | 28 | 21 | 70 | 70 |
| % PEO units grafted | 0.80% | 4.41% | 2.55% | 0.21% | 0.28% | 1.26% | 0.52% | 0.80% | 3.75% | 5.83% |
| Surface Energy: Nonpolar (mJ/m$^2$) | 40.6 | 35.8 | 35.5 | 33.1 | 41.6 | 43.0 | 44.0 | 41.0 | 40.3 | 37.1 |
| Surface Energy: Polar (mJ/m$^2$) | 8.7 | 2.7 | 1.3 | 0.5 | 21.5 | 21.1 | 17.2 | 17.2 | 3.9 | 0.1 |
| Surface Energy: Total (mJ/m$^2$) | 49.3 | 38.5 | 36.8 | 33.6 | 63.1 | 64.0 | 61.2 | 58.2 | 44.2 | 37.2 |

Preparation of Particles Comprising a Self-assembling Graft Copolymer and a Benefit Agent 1. Materials PEG-g-PVAc, amphiphilic graft copolymer, as per Example 1-10
Liquid detergent
Stuart SA8 vortex mixer (Bibby Scientific, Staffordshire, UK)
EchoTherm™ Orbital Mixing (Torrey Pines scientific, INC)

2. Procedure 2.1 Preparing a Matrix Containing an Active Substance

Weigh about 5 g of graft co-polymer (Examples 1-10 in Table 1) into a glass vial and screw the cap on. Set the EchoTherm™ block heater at 80° C. and wait until the polymer is melted. Place the vial on a balance and add one of the actives to be encapsulated e.g. hueing dye, enzyme solution, non-ionics, silicones, brightener solutions or combinations thereof. Mix with a Stuart SA8 vortex mixer (Bibby Scientific, Staffordshire, UK) at 2500 rpm until a homogeneous viscous liquid is obtained. The weight ratio is intended as the total weight of the benefits agent divided the total weight of the co-polymer.

2.2 Preparing Self-assembling Graft Copolymer Capsules

Take an adequate amount of sample from the vial of the mixed material prepared as in 2.1 and add to another vial containing the main product formulation e.g. Liquid Detergent such as Ariel so to have a 5% w/w concentration in the detergent. Mix with a Stuart SA8 vortex mixer at 600 rpm to disperse the self-assembling graft copolymer mixed with the benefit agent in the detergent matrix.

Addition of Benefit Agent Particles to Different Compositions

Upon addition, we observe the compositions under confocal microscope to assess the presence of the particles.

| | | | Formulation | | | |
|---|---|---|---|---|---|---|
| Material | Nonpolar Surface Energy/mJ/m2 | Polar Surface Energy Component/mJ/m2 | Fabric Enhancer Formulation 1 Free Water Content is 89% | Fabric Enhancer Formulation 1 with added citric acid and nonionic Free water content is 66% | Skin Care Formulation 1 Free water content is 61% | Hair Care Formulation 1 Free water content is 86% |
| Perfume + polymer according to Ex. 4 | 33.1 | 0.5 | Visible particles | Visible particles | Visible particles | Visible particles |
| Perfume + polymer according to Ex. 1 | 40.6 | 8.7 | No visible particles | Visible particles | No visible particles | No visible particles |
| Comparative Polymer | | | No visible particles | No visible particles | No visible particles | No visible particles |

| | | | Formulation | | | |
|---|---|---|---|---|---|---|
| Material | Nonpolar Surface Energy/mJ/m2 | Polar Surface Energy Component/mJ/m2 | Liquid Detergent Formulation 1 Free water content is 10% | Liquid Detergent Formulation 2 Free water content is 38% | Liquid Detergent Formulation 3 Free water content is 69% (Na LAS* 0%) | Liquid Detergent Formulation 4 Free water content is 67% (Na LAS* 3.5%) |
| Perfume + polymer according to Ex. 4 | 33.1 | 0.5 | Visible particles | Visible particles | Visible particles | |
| Hueing dye + polymer according to Ex. 1 | 40.6 | 8.7 | Visible particles | Visible particles | No visible particles | Visible particles (multi-core) FIG. 2 |
| Perfume + polymer according to Ex. 1 | 40.6 | 8.7 | Visible particles | Visible particles | No visible particles | Visible particles (multi-core) FIG. 2 |
| Perfume + polymer according to Ex. 6 | 43.1 | 21.0 | Visible particles | No visible particles | No visible particles | |
| Comparative Polymer - PVOH | | | No visible particles | No visible particles | No visible particles | |

| Objective | Particle Architecture | Polymer | Benefit Agent | level in Polymer | Matrix or FP | % Free water | self assembled |
|---|---|---|---|---|---|---|---|
| form polymer capsules, nil benefit agent | Matrix-like | Graft co-polymer of 40% PEG6000 and 60% PVAc, Mw 27K | none | 0 | Liquid Detergent Formulation 1 | 10% | yes |
| | Matrix-like | Sokalan PG101** | None | 0 | Liquid Detergent Formulation 1 | 10% | yes |
| | Multi-core | Graft co-polymer of 40% PEG6000 and 60% PVAc, Mw 27K | None | 0 | Liquid Detergent Formulation 2 | 38% | yes |
| | Multi-core | Sokalan PG101** | None | 0 | Liquid Detergent Formulation 2 | 38% | yes |
| | Matrix-like | Sokalan HP22 *** | None | 0 | Liquid Detergent Formulation 1 | 10% | yes |
| | Matrix-like | Ex. 1 | None | 0 | Liquid Detergent Formulation 1 | 10% | yes |

-continued

| | Particle Structure | Polymer | Other Additive | Other Additive Level | Product | Product Water level | Stability |
|---|---|---|---|---|---|---|---|
| | Matrix-like | Ex. 2 | None | 0 | Liquid Detergent Formulation 1 | 10% | yes |
| | Matrix-like | Ex. 3 | None | 0 | Liquid Detergent Formulation 1 | 10% | yes |
| | Matrix-like | Ex. 4 | None | 0 | Liquid Detergent Formulation 1 | 10% | yes |
| | Matrix-like | Ex. 5 | None | 0 | Liquid Detergent Formulation 1 | 10% | yes, marginal |
| | Matrix-like | Ex. 6 | None | 0 | Liquid Detergent Formulation 1 | 10% | yes, marginal |
| | Matrix-like | Ex. 7 | None | 0 | Liquid Detergent Formulation 1 | 10% | yes, marginal |
| | Matrix-like | Ex. 8 | None | 0 | Liquid Detergent Formulation 1 | 10% | yes, marginal |
| | Nothing | Graft co-polymer of 40% PEG6000 and 60% PVAc, Mw 27K | None | 0 | Liquid Detergent Formulation 3 | 69% | no |
| | Matrix-like | Ex. 3 | None | 0 | Liquid Detergent Formulation 3 | 69% | yes |
| | Matrix-like | Sokalan PG101** | None | 0 | L'Oreal Shampoo | 77% | Yes |
| | Multicore | Ex. 4 | None | 0 | Olaz Wrinkle | 61% | yes |
| | | Ex. 4 | None | 0 | Pantene Conditioner | 86% | yes |
| Perfume | Matrix-like | Sokalan PG101** | Hexarose | 20% | Liquid Detergent Formulation 1 | 10% | yes |
| | Matrix-like | Ex. 4 | Perfume Oil | 20, 40, 60, 80% | Fabric Enhancer Formulation 1 | 89% | yes |
| Silicone | Matrix-like | Sokalan PG101** | Silfoam SD168 (Wacker) | | Liquid Detergent Formulation | 40% | Yes |

*Na LAS sodium alkyl benzene sulfonate with a chain length $C_{11-13}$
**Supplied ex BASF, Mixture of 70% Graft co-polymer of 40% PEG6000 and 60% PVAc, Mw 27K, 20% Lutensol XL100 (BASF), 7% water and 3% tripropylene glycol
*** Supplied ex BASF, Graft co-polymer of 40% PEG6000 and 60% PVAc The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect o the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
    a) benefit agent delivery particles,
    said benefit agent delivery particles being self-assembling graft co-polymer capsules,
    said benefit agent delivery particles comprising at least one self assembling graft co-polymer and a benefit agent, said benefit agent being encapsulated in said self assembling graft co-polymer, and/or being partially embedded in said self assembling graft co-polymer, wherein said self assembling graft co-polymer comprises a co-polymer of polyalkylene glycol and vinyl acetate, where said co-polymer comprises a polyalkylene glycol backbone and vinyl acetate moieties that are covalently attached to said polyalkylene glycol backbone;
    b) an adjunct material; and
    c) a free water content of about 96% or less.

2. A composition according to claim 1, wherein said self-assembling graft co-polymer having hydrodynamic diameter of from about 10 nanometers to about 100 nanometers.

3. A composition according to claim 1, wherein said composition is selected from the group consisting of:
    (i) a unit dose composition comprising free water content of from about 5% to about 10%;
    (ii) a liquid detergent comprising free water content of from about 10% to about 70%;
    (iii) a liquid fabric enhancer comprising free water content of from about 80% to about 95%;
    (iv) a surface care cleaning composition comprising free water content of from about 85% to about 96%;
    (v) a skin care composition comprising free water content of from about 20% to about 96%; and
    (vi) a hair cleaning and/or conditioning composition comprising free water content of from about 20% to about 96%.

4. A composition according to claim 1, wherein said benefit agent delivery particles have a self-assembly index of from 1 to about 100 and/or a SAXS index of from 1 to about 100.

5. A composition according to claim 1, wherein said benefit agent is perfume.

6. A composition according to claim 1, wherein said benefit agent delivery particles are characterized by a particle structure selected from the group consisting of: matrix-like capsules, core-shell capsules, multiple-core capsules, and mixtures thereof.

7. Benefit agent delivery particles comprising a benefit agent and at least one self-assembling graft co-polymer, wherein said benefit agent delivery particles have a Dissolution Index of 1, a self-assembly index of from 1 to about 100, and/or a SAXS index of from 1 to about 100,
said benefit agent delivery particles being self-assembling graft co-polymer capsules,
wherein said self-assembling graft co-polymer comprises a co-polymer of polyalkylene glycol and vinyl acetate, where said co-polymer comprises a polyalkylene glycol backbone and vinyl acetate moieties that are covalently attached to said polyalkylene glycol backbone.

8. Benefit agent delivery particles of claim 7, wherein said benefit agent particles comprise at least one region comprising benefit agent being encompassed within said self-assembling graft co-polymer and/or being partially embedded within said self-assembling graft co-polymer.

9. Benefit agent delivery particles according to claim 7, wherein said benefit agent particles have a structure selected from the group consisting of:
a) a benefit agent delivery particle comprising a single region of benefit agent that is embedded in said self-assembling graft co-polymer;
b) a benefit agent delivery particle comprising at least two regions of benefit agent that are embedded in said self-assembling graft co-polymer;
c) a benefit agent delivery particle comprising at least one region of benefit agent that are at least partially embedded on the surface said self-assembling graft co-polymer;
d) a benefit agent delivery particle comprising a single region of benefit agent that is embedded in said self-assembling graft co-polymer and at least one region of benefit agent that is at least partially embedded on the surface said self-assembling graft co-polymer; and
e) a benefit agent delivery particle comprising at least two regions of benefit agent that are embedded in said self-assembling graft co-polymer and at least one region of benefit agent that is at least partially embedded on the surface said self-assembling graft co-polymer.

10. Benefit agent delivery particles according to claim 7, wherein said benefit agent particles have at least one particle having:
a) a diameter of from about 0.5 microns to about 5000 microns;
b) a diameter of from about 0.01 microns to about 0.5 microns; or
c) a diameter of from about 250 microns to about 10,000 microns.

11. Benefit agent delivery particles according to claim 7, wherein a weight ratio of said benefit agent to said self-assembling graft co-polymer is from about 1:20 to about 20:1.

12. Benefit agent delivery particles according to claim 7, wherein said benefit agent is selected from the group consisting of perfume raw materials, silicone oils, waxes, hydrocarbons, higher fatty acids, essential oils, lipids, skin coolants, vitamins, sunscreens, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape control agents, form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents, freshness extending agents, chlorine bleach odor control agents, dye fixatives, dye transfer inhibitors, color maintenance agents, optical brighteners, color restoration/rejuvenation agents, anti-fading agents, whiteness enhancers, antiabrasion agents, wear resistance agents, fabric integrity agents, anti-wear agents, antipilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti skin aging agents, facial contrast agents, anti dandruff agents, skin lightening agents, anti-acne agents, emollients, nonsteroidal anti-inflammatory agents, topical anaesthetics, artificial tanning agents, antimicrobial actives, anti-fungal actives, skin soothing agents, skin barrier repair agents, anti-skin atrophy actives, lipids, sebum inhibitors, skin sensates, protease inhibitors, anti-itch agents, desquamation enzyme enhancers, anti-glycation agents, and mixtures thereof.

13. Benefit agent delivery particles according to claim 7, wherein said benefit agent is selected from the group consisting of enzymes, bleaching systems, silicones, perfumes, fabric hueing agents, and mixtures thereof.

14. Benefit agent delivery particles according to claim 7, wherein said benefit agent is silicone.

15. Benefit agent delivery particles according to claim 7, wherein said benefit agent is perfume.

16. Benefit agent delivery particles according to claim 7, wherein said benefit agent is leuco dye.

17. Benefit agent delivery particles according to claim 7, wherein said self-assembling graft co-polymer has a surface energy of from about 20 to about 90.

18. Benefit agent particles according to claim 7, wherein said self-assembling graft co-polymer comprises a co-polymer of polyalkylene glycol and vinyl acetate having:
(i) a weight-average molecular weight of from about 2000 Daltons to about 250,000 Daltons, and
(ii) a ratio of polyalkylene glycol to vinyl acetate moieties of from about 5:1 to about 1:10.

19. Benefit agent particles according to claim 7, wherein said self-assembling graft co-polymer comprises a co-polymer of polyalkylene glycol and vinyl acetate having from 1 to about 10 vinyl acetate grafts per polyalkylene glycol backbone.

20. Benefit agent particles according to claim 7, wherein said self-assembling graft co-polymer comprises polyalkylene glycol and at least one monomer selected from the group consisting of vinyl esters, alkyl acrylates, alkyl methacrylates, alkyl acrylamides, alkyl methacrylamides, styrenes, halogenated olefins, and mixtures thereof.

21. A composition comprising benefit agent particles according to claim 7, wherein said composition comprises a free water content of about 96% or less.

22. A composition comprising benefit agent particles according to claim 7, wherein said composition is a unit dose composition comprising free water content of from about 5% to about 10%.

23. A composition comprising benefit agent particles according to claim 7, wherein said composition is a liquid detergent comprising free water content of from about 10% to about 70%.

24. A composition comprising benefit agent particles according to claim 7, wherein said composition is a liquid fabric enhancer comprising free water content of from about 80% to about 95%.

25. A composition comprising benefit agent particles according to claim 7, wherein said composition is a surface care cleaning composition comprising free water content of from about 85% to about 96%.

26. A composition comprising benefit agent particles according to claim 7, wherein said composition is a skin care composition comprising free water content of from about 20% to about 96%.

27. A composition comprising benefit agent particles according to claim 7, wherein said composition is a hair cleaning and/or conditioning composition comprising free water content of from about 20% to about 96%.

28. A composition according to claim 21, wherein said self-assembling graft co-polymer has a hydrodynamic diameter of from about 10 nanometers to about 100 nanometers.

29. A composition according to claim 21, wherein said composition further comprises, based on total composition weight, from about 0.1% to about 25% of a surfactant selected from the group consisting of a cationic surfactant, an anionic surfactant, a nonionic surfactant, and mixtures thereof.

30. A composition according to claim 29, wherein said surfactant comprises a nonionic surfactant.

31. A composition according to claim 21, wherein said composition further comprises a water binding agent.

32. A composition according to claim 31, wherein said water binding agent is selected from the group consisting of organic acids, salts of organic acids, humectants, desiccants, natural sugar substitutes, artificial sugar substitutes, hydrogels, and mixtures thereof.

33. A composition according to claim 21, wherein said composition comprises, based on total composition weight, from about 5% to about 20% of free water content, and wherein said composition is encased in a film.

34. A composition according to claim 21, wherein said composition comprises a liquid and/or gel and a film, said film encasing said liquid and/or gel, optionally said liquid or gel comprises a suspended solid.

35. A composition according to claim 21, wherein said composition comprises, based on total composition weight, from about 5% to about 95% water and from about 0.5% to about 25% of a builder.

36. A composition according to claim 21, wherein said composition comprises a material selected from the group consisting of a hueing dye, a structurant, an additional perfume delivery system, and mixtures thereof.

37. A composition according to claim 21, wherein said composition comprises:
   a) a structurant selected from the group consisting of polysaccharides;
   b) a hueing dye selected from the group consisting of small molecule dyes, polymeric dyes, dye-clay conjugates, and organic and inorganic pigments; and/or
   c) an additional perfume delivery comprising a material selected from the group consisting of a second microcapsule, a polymer assisted delivery system; a molecule-assisted delivery system; a fiber-assisted delivery system; a cyclodextrin delivery system; a starch encapsulated accord; and an inorganic carrier delivery system.

38. A composition according to claim 21, wherein said composition has a viscosity of from 1 to 1500 centipoises (1-1500 mPa*s) at 20 $s^{-1}$ and 21° C.

39. Benefit agent delivery particles according to claim 7, wherein said benefit agent delivery particles are characterized by a particle structure selected from the group consisting of: matrix-like capsules, core-shell capsules, multiple-core capsules, and mixtures thereof.

* * * * *